(12) United States Patent
Buan et al.

(10) Patent No.: US 11,813,396 B2
(45) Date of Patent: Nov. 14, 2023

(54) NEGATIVE PRESSURE TREATMENT INCLUDING MECHANICAL AND CHEMICAL PUMP

(71) Applicant: Aatru Medical, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US)

(73) Assignee: AATRU MEDICAL, LLC, Cleveland, OH (US)

( * ) Notice: Subject to any disclaimer, the term of this patent is extended or adjusted under 35 U.S.C. 154(b) by 247 days.

(21) Appl. No.: 17/167,268

(22) Filed: Feb. 4, 2021

(65) Prior Publication Data

US 2021/0154376 A1 May 27, 2021

Related U.S. Application Data

(63) Continuation of application No. PCT/US2019/012298, filed on Jan. 4, 2019.
(Continued)

(51) Int. Cl.
*A61M 1/00* (2006.01)
*A61F 13/02* (2006.01)

(52) U.S. Cl.
CPC .......... *A61M 1/962* (2021.05); *A61F 13/0206* (2013.01); *A61F 13/0216* (2013.01); *A61M 1/782* (2021.05)

(58) Field of Classification Search
CPC ........ A61M 1/962; A61M 1/782; A61M 1/80; A61M 1/918; A61M 1/985; A61M 1/81;
(Continued)

(56) References Cited

U.S. PATENT DOCUMENTS 5,676,650 A * 10/1997 Grieshaber ............. A61M 1/77
417/205
6,890,553 B1 5/2005 Sun et al.
(Continued)

FOREIGN PATENT DOCUMENTS

CN 112601573 4/2021
JP 2010-506691 3/2010
(Continued)

OTHER PUBLICATIONS

Ruiz, Nasal Aspirator Device, Jul. 12, 2018, Machine Translation (Year: 2018).*
(Continued)

*Primary Examiner* — Jessica Arble
*Assistant Examiner* — Brandon W. Levy
(74) *Attorney, Agent, or Firm* — Rankin, Hill & Clark LLP

(57) ABSTRACT

A negative pressure assembly includes a drape, a sealing element, a reactor, and a mechanical pump assembly. The drape covers a dressing site on a patient and seals against the skin upon application of a vacuum while maintaining a negative pressure underneath the drape. When applied to the skin, the sealing element cooperates with the drape to define an enclosed volume covered by the drape and surrounded by the sealing element. The reactor is located with respect to the drape and the sealing element to be in fluid communication with the enclosed volume when the drape is covering the dressing site and is configured to react with and consume a selected gas found in air. The mechanical pump assembly is connectable to the enclosed volume and has a pump chamber in fluid communication with the enclosed volume to draw air from the enclosed volume into the pump chamber.

11 Claims, 14 Drawing Sheets

Related U.S. Application Data

(60) Provisional application No. 62/724,159, filed on Aug. 29, 2018.

(58) Field of Classification Search
CPC .... A61M 2205/0277; A61M 2205/073; A61M 2209/06; A61M 27/00; A61M 1/74; A61M 1/915; A61M 1/96; A61M 1/85; A61M 1/912; A61F 13/0216; A61F 13/0206; A61F 13/00068; A61F 17/00; A61F 13/0253; A61F 2013/00174; A61H 2201/1238; A61H 9/0057; A61H 2201/1246; A61H 2201/5056; A61H 2201/0278; A61H 2201/165; A61P 17/02; F04B 19/006; A61L 15/425
See application file for complete search history.

(56) References Cited

U.S. PATENT DOCUMENTS

| | | | |
|---|---|---|---|
| 7,615,036 | B2 | 11/2009 | Joshi et al. |
| 8,323,264 | B2 | 12/2012 | Weston et al. |
| 9,283,118 | B2 | 3/2016 | Locke et al. |
| 10,046,095 | B1 | 8/2018 | Middaugh |
| 2004/0064132 | A1 | 4/2004 | Boehringer |
| 2004/0073151 | A1* | 4/2004 | Weston ............... A61M 1/982 602/41 |
| 2005/0070835 | A1 | 3/2005 | Joshi |
| 2007/0055209 | A1* | 3/2007 | Patel ................ A61F 13/00063 604/315 |
| 2007/0265585 | A1 | 11/2007 | Joshi |
| 2007/0265586 | A1 | 11/2007 | Joshi |
| 2008/0033330 | A1* | 2/2008 | Moore ................. A61M 1/912 602/54 |
| 2008/0183119 | A1 | 7/2008 | Joshi |
| 2008/0234726 | A1 | 9/2008 | Biddle |
| 2009/0299251 | A1 | 12/2009 | Buan |
| 2010/0137775 | A1 | 6/2010 | Hu |
| 2011/0009838 | A1 | 1/2011 | Greener |
| 2011/0045222 | A1 | 2/2011 | Peters |
| 2011/0224633 | A1* | 9/2011 | Robinson .......... A61F 13/00068 604/319 |
| 2012/0078153 | A1 | 3/2012 | Russell |
| 2013/0053795 | A1* | 2/2013 | Coulthard ......... A61F 13/00068 604/319 |
| 2013/0102979 | A1 | 4/2013 | Coulthard |
| 2013/0131616 | A1* | 5/2013 | Locke ................. A61M 1/918 604/319 |
| 2013/0331823 | A1 | 12/2013 | Askem |
| 2015/0057625 | A1 | 2/2015 | Coulthard |
| 2015/0191845 | A1 | 7/2015 | Scherson et al. |
| 2017/0143882 | A1 | 5/2017 | Smith |
| 2018/0318137 | A1 | 11/2018 | Donda |
| 2019/0091382 | A1 | 3/2019 | Middaugh |
| 2019/0159938 | A1* | 5/2019 | Askem ................. A61M 1/784 |

FOREIGN PATENT DOCUMENTS

| | | | |
|---|---|---|---|
| WO | 2008/049029 | 4/2008 | |
| WO | 2017/019669 | 2/2017 | |
| WO | 2017/075331 | 5/2017 | |
| WO | WO-2018127613 A1 * | 7/2018 | ............ A61M 1/00 |

OTHER PUBLICATIONS

International Search Report filed in PCT/US19/12298 dated Jun. 11, 2019.

* cited by examiner

NEGATIVE PRESSURE TREATMENT INCLUDING MECHANICAL AND CHEMICAL PUMP

BACKGROUND

Negative pressure therapy is a therapeutic treatment that utilizes negative pressure for skin treatments and restorative purposes. Negative pressure is a term used to describe a pressure that is below normal atmospheric pressure. Negative pressure therapy is utilized for several sites on the skin, such as a wound or an incision. Furthermore, negative pressure therapy is useful to manage wounds with complex healing concerns. Additionally, negative pressure therapy could also be used for cosmetic purposes like removing wrinkles.

Generally, negative pressure therapy is achieved by maintaining a reduced pressure beneath a dressing on a dressing site. A vacuum generation source, such as a pump, applies reduced pressure to the inside of the dressing on the dressing site. However, when a vacuum source that operates using a chemical reaction is first activated, a desirable negative pressure may not be obtained for the first few minutes of the operation of the vacuum source. As a result, if the dressing is not properly sealed at the beginning of the negative pressure therapy, an indication that the dressing is not sealed may not be noticeable for a few minutes. Furthermore, when a reduced pressure is finally obtained, the negative pressure may be susceptible to decreasing below a target pressure range for the negative pressure therapy (e.g., too much vacuum is applied on the skin). When the negative pressure decreases below the target pressure range, the dressing may be uncomfortable for the patient.

SUMMARY

In view of the foregoing, a negative pressure assembly includes a drape, a sealing element, a reactor, and a mechanical pump assembly. The drape covers a dressing site on a patient and when sealed against the skin upon application of a vacuum is capable of maintaining a negative pressure underneath the drape. When applied to the skin, the sealing element cooperates with the drape to define an enclosed volume covered by the drape and surrounded by the sealing element. The reactor is configured to react with and consume a selected gas found in air, and is located with respect to the drape and the sealing element to be in fluid communication with the enclosed volume when the drape is covering the dressing site. The mechanical pump assembly is fluidly connectable to the enclosed volume and has a pump chamber in fluid communication with the enclosed volume to draw air from the enclosed volume into the pump chamber.

The negative pressure assembly described above may further include a dressing including the drape and an absorbent material. Additionally, the reactor may be disposed in the dressing. Furthermore, a relief valve may be disposed on the dressing. The relief valve is in fluid communication with the enclosed volume and ambient. When a pressure differential between ambient and the enclosed volume is outside a predetermined pressure range, the relief valve allows gas from ambient to enter the enclosed volume.

The mechanical pump assembly can be connected to the dressing, and the pump chamber of the mechanical pump assembly is in fluid communication with the enclosed volume. The mechanical pump assembly can be connected to the dressing via a valve, a fitting, or a hose. The valve may be configured to allow gas to exit through the valve and into the pump chamber of the mechanical pump assembly while also preventing ambient air from entering into the enclosed volume through the valve. Alternatively, the valve may be a bidirectional valve configured to allow gas to exit through the valve when ambient pressure is below that of the enclosed volume and to allow gas from ambient to enter the enclosed volume through the valve when the pressure differential between ambient and the enclosed volume is outside a predetermined pressure range. Furthermore, the mechanical pump assembly may include a manually-actuated actuator and a biasing mechanism operatively connected with a movable pump element. When the manually-actuated actuator is actuated, the biasing mechanism moves the movable pump element. In result, air is drawn into the mechanical pump assembly. The biasing mechanism can be a spring, and the movable pump element can be a piston.

The negative pressure assembly described above may further include a chemical pump assembly including a chemical pump housing having a chamber. In this embodiment, the reactor is positioned in the chamber of the chemical pump housing instead of the dressing. Furthermore, the chemical pump assembly may include a diaphragm which moves toward the chamber to indicate when the chamber is under negative pressure. Additionally, the relief valve may alternatively be disposed on the chemical pump assembly instead of the dressing or may remain on the dressing.

The chemical pump housing may be connected to the dressing via a valve, a fitting, or a hose. Furthermore, the chemical pump assembly may be connected to a second dressing covering a second dressing site via a second valve, a second fitting, or the hose. The hose may be Y-shaped to connect the chemical pump assembly to the dressing and the second dressing at the same time. When the chemical pump housing is connected to the dressing, the chamber of the chemical pump assembly is in fluid communication with the enclosed volume. The hose may be retractable into the chemical pump assembly. Alternatively, the hose can be wound around a wrap element disposed on the chemical pump assembly. Also, when the chemical pump assembly is connected with the dressing via a fitting, the mechanical pump assembly may also be connected with the dressing via the fitting when the chemical pump assembly is not connected to the dressing via the fitting. Alternatively, the chemical pump assembly and the mechanical pump assembly may be connected to the dressing via separate valves, fittings, and/or hoses.

In still another embodiment, the mechanical pump assembly can be connected to the chemical pump assembly. In result, the pump chamber of the mechanical pump assembly is in fluid communication with the enclosed volume via the chemical pump assembly. The mechanical pump assembly can be connectable with the chemical pump housing via a valve, a fitting, or a hose. In the embodiment with the valve, gas can exit through the valve and into the pump chamber while also preventing ambient air from entering the chamber through the valve.

A negative pressure assembly according to another embodiment includes a drape, a sealing element, a valve, and a mechanical pump assembly. The drape covers a dressing site on a patient and is capable of maintaining a negative pressure underneath the drape when sealed against the patient's skin upon application of a vacuum. The sealing element cooperates with the drape when applied to the skin to define an enclosed volume covered by the drape and surrounded by the sealing element. The valve is disposed on the drape and has a first operating state in which gas exits the enclosed volume through the valve and a second operating state in which gas is precluded from exiting the enclosed volume through the valve. The mechanical pump assembly includes a pump chamber fluidly connectable to the enclosed volume through the valve when the valve is in the first operating state. The mechanical pump assembly is also configured to draw air from the enclosed volume into the pump chamber when fluidly connected with the enclosed volume.

The negative pressure assembly may further include a dressing including the drape, the sealing element, and an absorbent material. The mechanical pump assembly is connectable to the dressing through the valve so that the pump chamber is in fluid communication with the enclosed volume. The negative pressure assembly may also include a reactor located with respect to the drape and the sealing element so that the reactor is in fluid communication with the enclosed volume when the drape is covering the dressing site. The reactor reacts with a selected gas found in air and consumes the selected gas. In one embodiment, the reactor is disposed in the dressing. In another embodiment, the negative pressure assembly further includes a chemical pump assembly having a chemical pump. housing in which the reactor is disposed in the chemical pump housing.

Furthermore, a relief valve may be disposed on the dressing. The relief valve is in fluid communication with the enclosed volume and ambient. The relief valve allows gas from ambient to enter the enclosed volume through the relief valve when a pressure differential between ambient and the enclosed volume is outside a predetermined pressure range. Alternatively, the valve may be a bidirectional valve that allows gas to exit through the valve when ambient pressure is below that of the enclosed volume and allows gas from ambient to enter the enclosed volume through the valve when the pressure differential between ambient and the enclosed volume is outside a predetermined pressure range. The predetermined pressure range may be between 50 and 200 mmHg below atmospheric pressure.

Additionally, the mechanical pump assembly may include a manually-actuated actuator and a biasing mechanism operatively connected with a movable pump element. The actuation of the manually-actuated actuator results in the biasing mechanism moving the movable pump element. In result, air is drawn into the mechanical pump assembly. The biasing mechanism may be a spring, and the movable pump element may be a piston. A hose may also be retractable into the mechanical pump assembly. Alternatively, the hose may be wound around a wrap element on the mechanical pump assembly. The mechanical pump assembly may further be connected to a second dressing covering a second dressing site via a valve, a fitting, or a hose.

DETAILED DESCRIPTION

Figure 1:
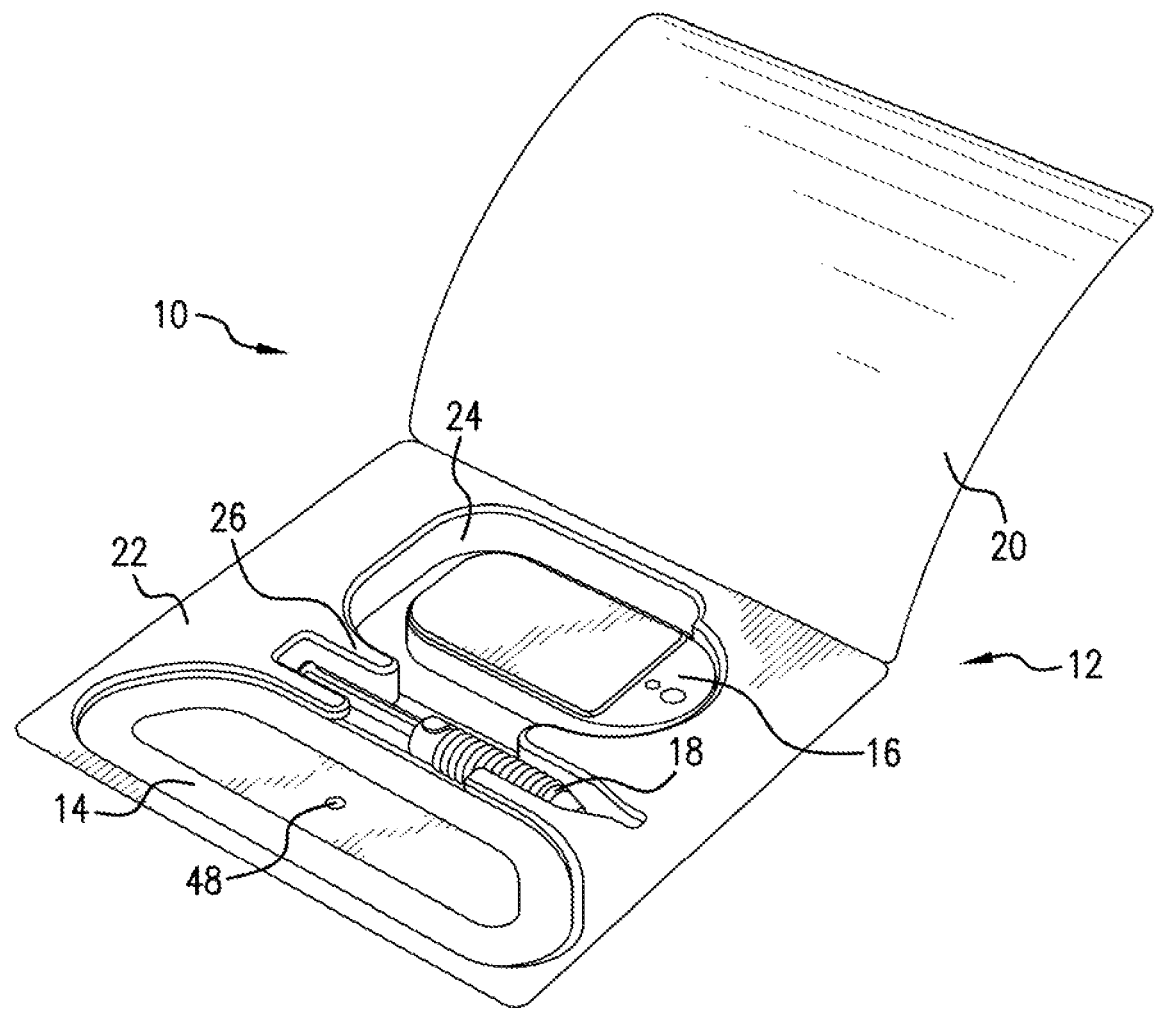
FIG. 1 is a perspective view of a negative pressure kit.

FIG. 1 depicts a negative pressure kit 10 useful for negative pressure therapy. Negative pressure described herein is pressure below atmospheric pressure. The negative pressure kit 10 includes a tray kit 12 and a negative pressure assembly. In the embodiment depicted in FIG. 1, the negative pressure assembly includes at least one dressing 14, a chemical pump assembly 16, and a mechanical pump assembly 18.

The tray kit 12 comprises a top cover 20 and a bottom cover 22. At least one recess 24 may be provided on the bottom cover 22 for storing the at least one dressing 14, the chemical pump assembly 16, and the mechanical pump assembly 18. Spacer walls 26 can be added to maintain space between the top cover 20 and bottom cover 22 when the tray kit 12 is closed. The spacer walls 26 can at least partially surround the perimeter of the at least one recess 24. The bottom cover 22 may further include securing elements for securing the components in the at least one recess 24. Also, the tray kit 12 may comprise a closing element for keeping the top cover 20 and bottom cover 22 closed, and may further include locking attachments for locking the tray kit 12 when the tray kit 12 is closed.

Figure 2:
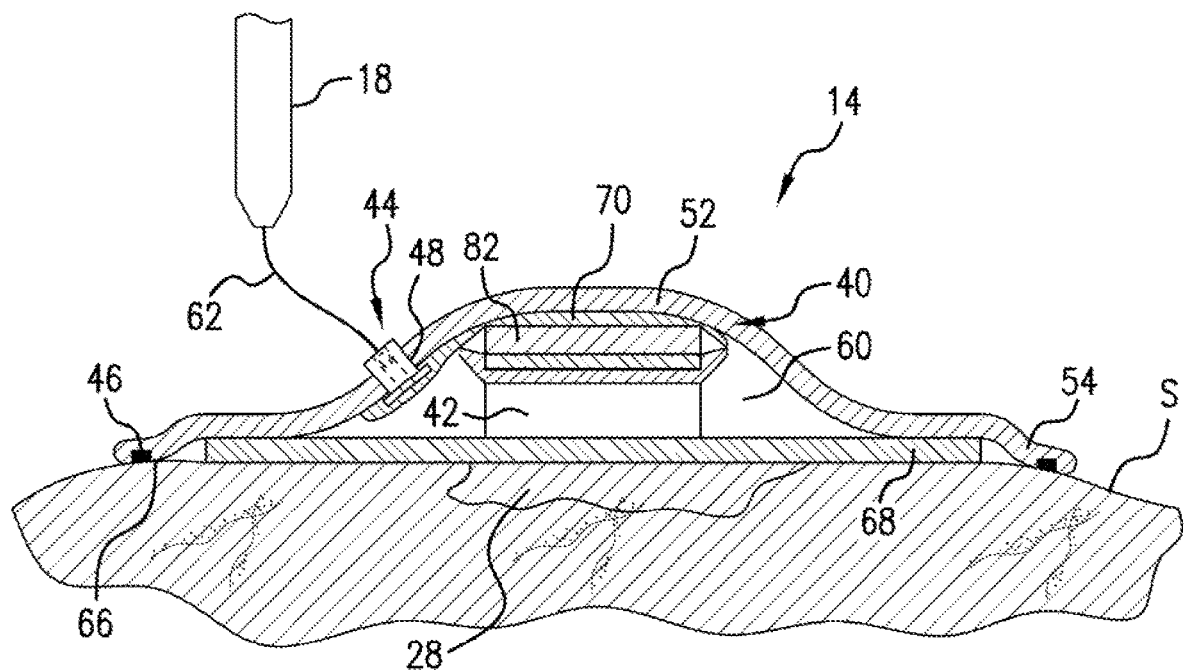
FIG. 2 is a schematic cross-sectional view of a dressing and a mechanical pump assembly of the negative pressure kit according to one embodiment.

With reference to FIG. 2, the dressing 14 is placed over a dressing site 28 on a patient's skins. The dressing site 28 can be, but is not limited to, a wound, an incision, or skin where there is no wound or incision. In the illustrated embodiment, the dressing 14 includes a drape 40, a wicking or absorbent element 42 and a fitting 44. The dressing 14 can include further components, such as a sealing element 46, and can be similar construction to the dressings described in U.S. application Ser. No. 16/114,813 and/or PCT/US2016/059364. The drape 40 can be made from a flexible material and can be made from a thin, flexible elastomeric film. Examples of such materials include polyurethane or polyethylene films. The drape 40 can include at least one opening 48 (see FIG. 1), which can cooperate with the fitting 44. The drape 40 in the illustrated embodiment is a thin film capable of maintaining a negative pressure underneath the drape 40 when sealed against the skin upon application of a vacuum when the opening 48 is not in communication with ambient.

The drape 40 further comprises a drape top 52 and a drape edge 54. The drape top 52 and the drape edge 54 can be made from one continuous piece or multiple pieces fused together. The drape edge 54 is placed around the dressing site 28, and the drape top 52 covers the dressing site 28. The drape 40 can be made in a variety of shapes and sizes to cover a variety of dressing sites 28. The opening 48 extends through the drape top 52.

With continued reference to FIG. 2, the sealing element 46 cooperates with the drape 40 and the skin S to create an enclosed volume 60 defined between the drape 40 and the dressing site 28 and surrounded by the sealing element 46. The sealing element 46 can be separate from the dressing 14 or a component of the dressing 14. The sealing element 46 functions like a gasket, as the sealing element 46 prevents fluid (including air) from escaping between the drape 40 and the skin S. When properly sealed, air or select gases found in air can selectively exit the dressing 14 through the at least one opening 48 and fitting 44. Thus, the sealing element 46 helps maintain negative pressure within the dressing 14. The sealing element 46 can be made from a material such as silicone or a hydrogel material.

The dressing 14 may further include a wound contact layer 68. The drape top 52 covers the wound contact layer 68 and/or the wicking or absorbent element 42. The wound contact layer 68 can be made of an elastomeric material, such as a polymeric material that has rubber-like properties. Furthermore, the wound contact layer 68 can be an elastomeric material that is a thin, flexible elastomeric film. Some examples of such materials include a silver coated nylon, a perforated silicone mesh, or other materials that will not stick to the patient's tissue. The wound contact layer 68 contacts the dressing site 28. The wound contact layer 68 can include at least one opening to cooperate with the wicking element 42 to retain exudate traveling from the dressing site 28 into the enclosed volume 60. The sealing element 46 can also be disposed on the side of the wound contact layer 68 that contacts the dressing site 28 (or the wicking element 42 if the wound contact layer 68 is not included).

A drape release liner (not shown) is disposed on the bottom surface of the drape edge 54. The drape release liner is removed before the dressing 14 is applied to the dressing site 28. When the drape release liner is removed, an adhesive 66 on the bottom surface of the drape edge 54 is exposed. As the dressing 14 is placed on the patient, the adhesive 66, which can be an acrylic-based adhesive that is distinct from the sealing element 46, secures the drape edge 54 to the patient's skin S around the dressing site 28. Thus, contact is maintained between the drape edge 54 and the skin S.

The wicking or absorbing element 42 is made from an absorbent material that is capable of absorbing exudate from the dressing site 28. The wicking element 42 can be made from super absorbent polymers, absorbent beads, foams, or natural absorbents. Also, the wicking element 42 can provide appropriate voids for gases found in air so that reduced pressure can be maintained. For example, the wicking element 42 can be made from a relatively more rigid foam as compared to the drape 40 so that gas voids are maintained while absorbing exudate from the wound. The wicking element 42 could also be made from the superabsorbent polymers described above that expand and form gas voids, for example between adjacent beads, to provide aforementioned volume control. The wicking element 42 can also be a hydroactive wound pad available under the trademark Vilmed®, which chemically absorbs exudate and precludes the exudate from passing through the wicking element toward the vacuum source unlike a sponge.

The dressing 14 can also include an air permeable liquid impervious membrane 70 covering the opening 48 in the drape top 52. In an embodiment, the air permeable liquid impervious membrane 70 is disposed on the bottom surface of the drape top 52. Air is allowed to travel through the air permeable liquid impervious membrane 70, whereas liquid is prevented from traveling through the air permeable liquid impervious membrane 70. Therefore, exudate is not able to flow through the air permeable liquid impervious membrane 70. In another embodiment, the air permeable liquid impervious membrane 70 is disposed on the top surface of the drape top 52. Furthermore, FIG. 2 depicts a chemical pump 82 in the form of a reactor disposed in the dressing 14 beneath the drape 40. The chemical pump 82 can be located elsewhere, which will be described in more detail below.

Figure 3:
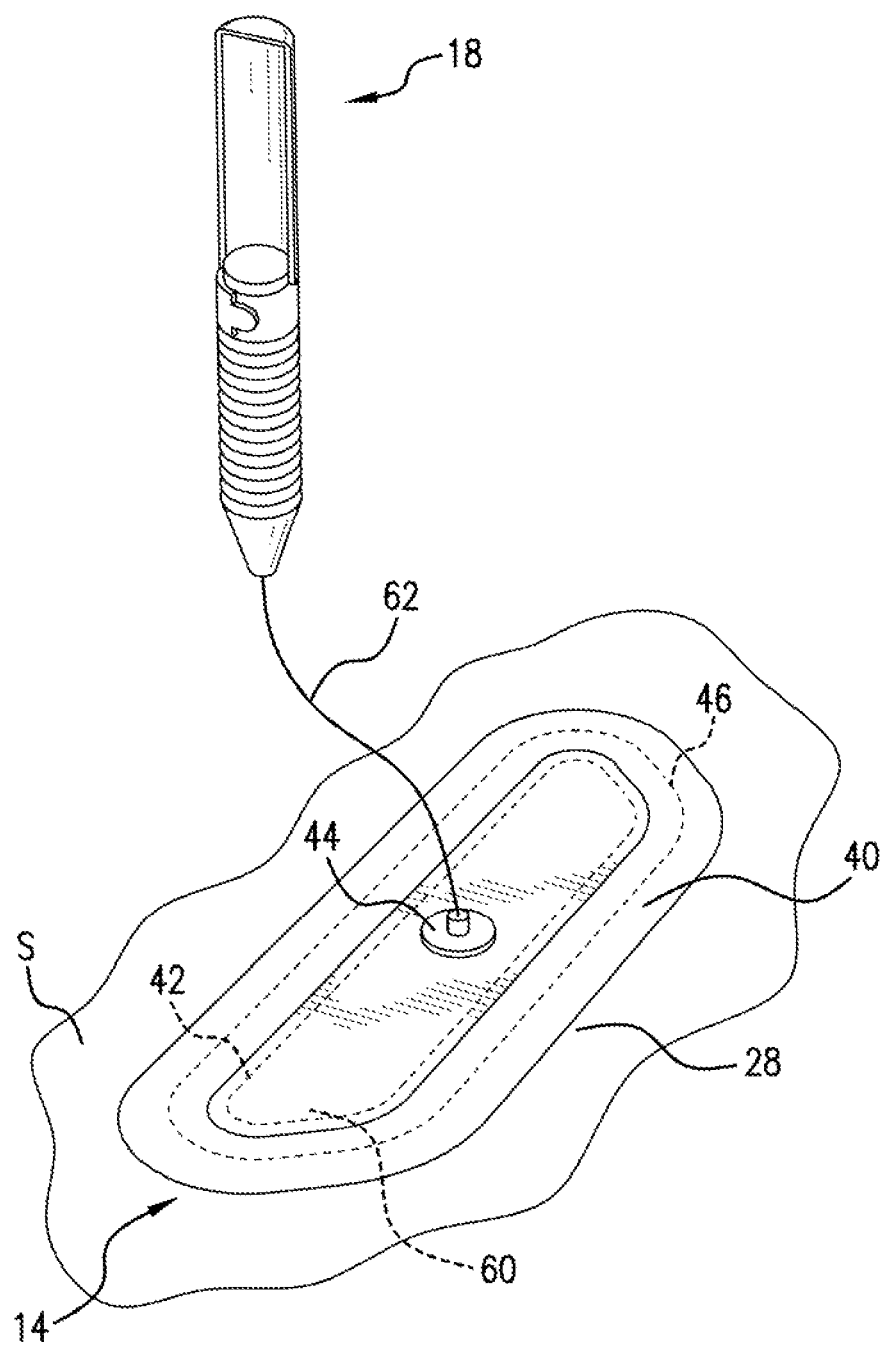
FIG. 3 is a perspective view of a dressing and a mechanical pump assembly.

FIG. 3 depicts the dressing 14 connected with the mechanical pump assembly 18 via a hose 62 (schematically depicted). When the mechanical pump assembly 18 is connected to the dressing 14, the mechanical pump assembly 18 is in fluid communication with the enclosed volume 60 via the fitting 44 in a manner described in more detail below. Actuation of the mechanical pump assembly 18 draws air from the enclosed volume 60 through the opening 48, fitting 44, and hose 62 into the mechanical pump assembly 18. As such, the sealing of the dressing 14 against the skin S can be checked in that the drape 40 would be drawn toward the skin S. The hose 62 can then be removed from the fitting 44, which would allow air into the enclosed volume 60 resulting in the enclosed volume 60 returning towards atmospheric pressure.

Figure 4:
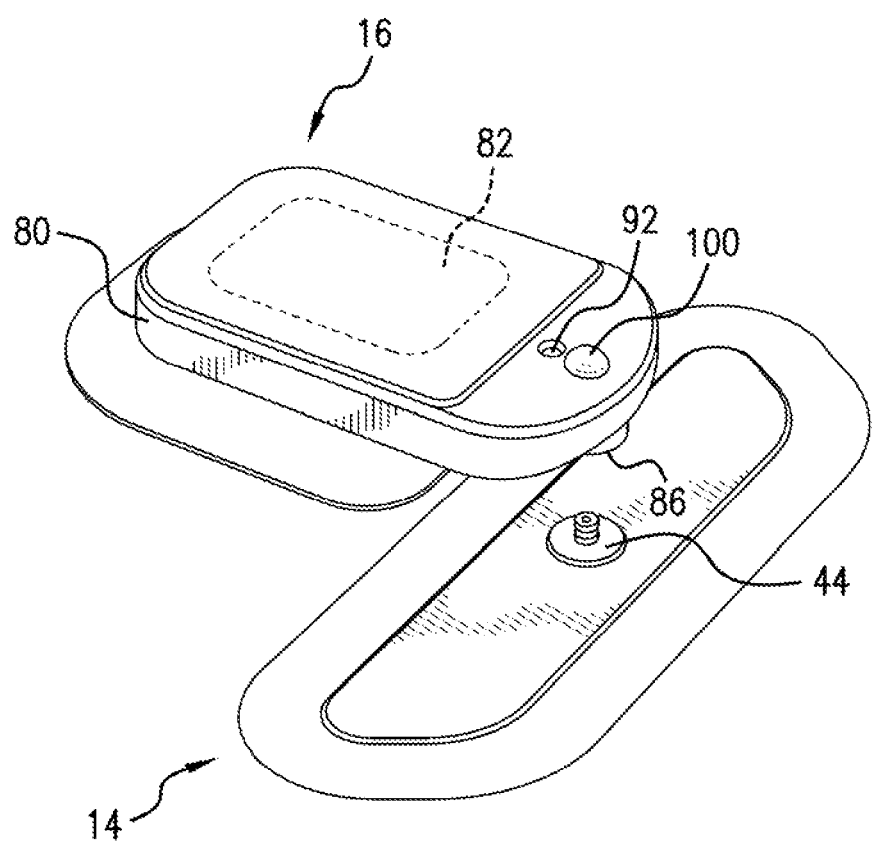
FIG. 4 is a perspective view of the dressing in FIG. 3 and a chemical pump assembly prior to connection of the chemical pump assembly to the dressing.

FIG. 4 depicts the dressing 14 and the chemical pump assembly 16. The chemical pump assembly 16 includes a chemical pump housing 80, a chemical pump 82 (shown in phantom in FIG. 4) positioned in a chamber 84 (see FIG. 5), and a lower opening 86 disposed on the bottom of the chemical pump housing 80 and in fluid communication with the chamber 84. When connected with the fitting 44, the chamber 84 in the chemical pump housing 80 is in fluid communication with the enclosed volume 60 via the lower opening 86, the at least one opening 48, and the fitting 44 on the drape 40. The chemical pump assembly 16 applies reduced pressure on the inside of the dressing 14 in a manner that will be described in more detail below.

The chemical pump 82 in the chemical pump assembly 16 is a reactor configured to react with a selected gas found in air. The chemical pump 82 is located with respect to the drape 40 and sealing element 46 so that the chemical pump 82 can be in fluid communication with the enclosed volume 60. The chemical pump 82 consumes the selected gas from the enclosed volume 60, thereby removing the gas and reducing the gas pressure. Examples of reactors that can be used in the chemical pump assembly 16 are described in US 2014/0109890A1 and PCT/US2016/059364. In the case of a therapeutic negative pressure system, utilized for wound care, the range of reported operating pressures, relative to standard atmospheric pressure of 760 mmHg, are −50 mmHg to −200 mmHg (absolute pressure of 560 to 710 mmHg). When the pressure is less than 560 mmHg, the at least one dressing 14 can become uncomfortable for the patient. When the pressure is above 710 mmHg, the negative pressure therapy may not be as effective compared to pressures below 710 mmHg. However, smaller target pressure ranges within the 560 to 710 mmHg may be desired. Thus, the reactor 82 can be configured to maintain a reduced pressure range within a predetermined target pressure range.

The chemical pump assembly 16 is configured to maintain a predefined chamber volume, as the chemical pump 82 consumes the selected gas from the enclosed volume 60. The size of the reactor 82 is dependent on the volume of the chamber 84, the hose 62 and the enclosed volume 60, among other factors. In another embodiment, the reactor 82 can be disposed in the dressing 14 instead of the chemical pump assembly 16, as depicted in FIG. 2. As a result, the chemical pump assembly 16 may be eliminated in the method of applying negative pressure within the dressing 14.

Figure 5:
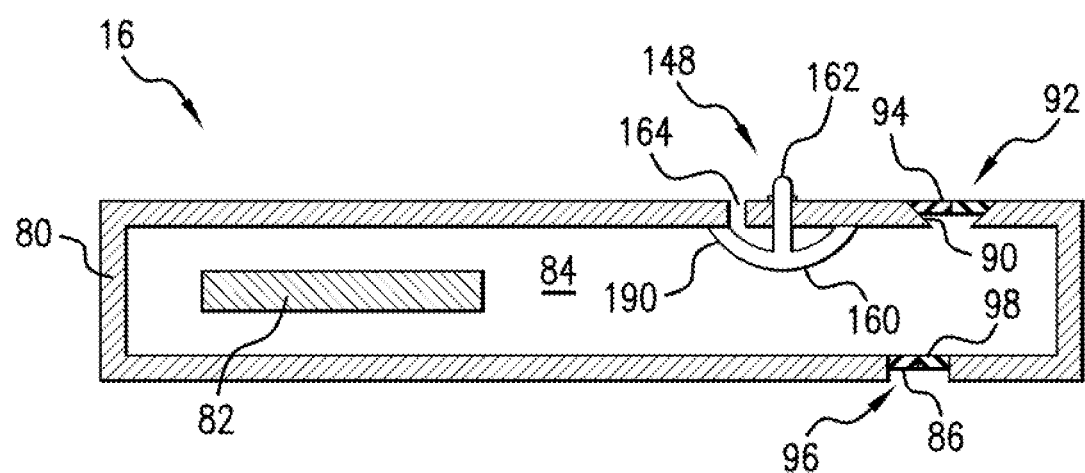
FIG. 5 is a schematic cross-sectional view of the chemical pump assembly according to one embodiment.

In the illustrated embodiment of FIG. 5, an upper opening 90, in which a first valve 92 is disposed, is provided on the top of the chemical pump housing 80. Additionally, the upper opening 90 and first valve 92 can be disposed on a side of the chemical pump housing 80 and elsewhere on the chemical pump housing 80. In another embodiment, a valve that operates similarly to the first valve 92 can be disposed on the dressing 14. The first valve 92 is configured to work with the mechanical pump assembly 18. In the first operating state, the first valve 92 allows air to exit the chamber 84 through the first valve 92 when the mechanical pump assembly 18 is inserted into the first valve 92. In the second operating state, the first valve 92 precludes ambient air from entering the chamber 84 through the upper opening 90 and first valve 92 when the mechanical pump assembly 18 is not inserted into the first valve 92. Examples of such valves include, but are not limited to, a spring-biased check valve and a valve comprising flaps. FIG. 5 depicts the first valve 92 having flaps 94. The flaps 94 on the first valve 92 are closed before the mechanical pump assembly 18 is introduced into the upper opening 90. No gas is allowed to escape through the upper opening 90 and the first valve 92 unless the mechanical pump assembly 18 is introduced. The flaps 94 on the first valve 92 return to the closed position by their resilient forces, as the mechanical pump assembly 18 is removed.

In the illustrated embodiment, a sealing member 96 is disposed on the bottom of the chemical pump housing 80. Also, the sealing member 96 can be disposed on a side of the chemical pump housing 80 and elsewhere on the chemical pump housing 80. In the illustrated embodiment, the sealing member 96 is positioned in the lower opening 86 and configured to work with the fitting 44. The sealing member 96 allows air to enter the chamber 84 through the lower opening 86 when the chemical pump assembly 16 is pressed onto and fitted with the fitting 44. The sealing member 96 prevents ambient air from entering the chamber 84 when the chemical pump assembly 16 is not fitted onto the fitting 44. FIG. 5 depicts the sealing member 96 having flaps 98. The flaps 98 on the sealing member 96 are closed before the chemical pump assembly 16 is fit onto the fitting 44. No gas is allowed to enter through the sealing member 96 unless the flaps 98 are moved from their initial closed position. Alternatively, the sealing member 96 can be foil or another member capable of being punctured when pressed against the fitting 44.

With reference to FIG. 4, a negative pressure indicator, which in the illustrated embodiment is a diaphragm 100, may be disposed on the chemical pump housing 80 to provide an indication to the user that the system is under negative pressure. Referring to FIG. 4, the diaphragm 100 can be dome shaped protruding out of the chemical pump housing 80 when the pressure in the chamber 84 is at or above a predetermined pressure, which can be atmospheric pressure. The diaphragm 100 can be made from an elastic material. As the pressure in the chemical pump assembly 16 or dressing 14 decreases below the target pressure range, the diaphragm 100 is drawn into the chemical pump housing 80. As the diaphragm 100 is drawn towards the inside of the chemical pump housing 80, the diaphragm 100 is inverted. When the diaphragm 100 is inverted, this provides an indication to the user that the system is under negative pressure. Alternatively, the indicator can be disposed on the dressing 14.

Figure 6:
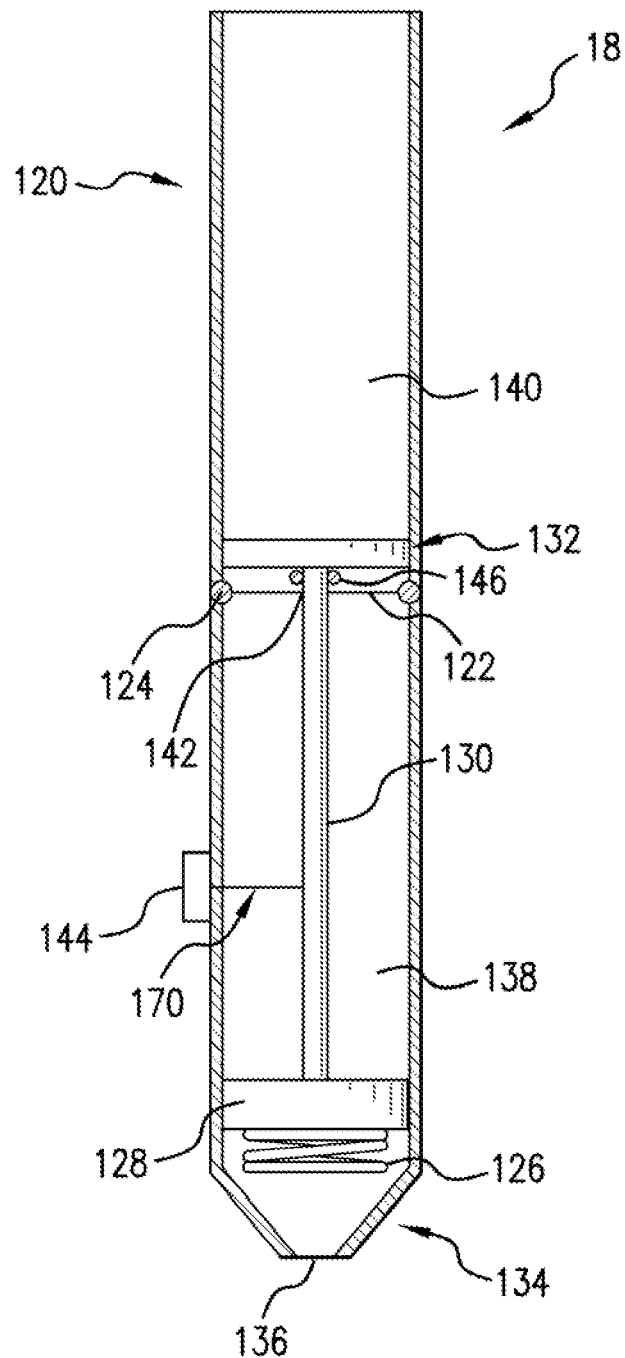
FIG. 6 is a schematic cross-sectional view of the mechanical pump assembly before actuation.
Figure 7:
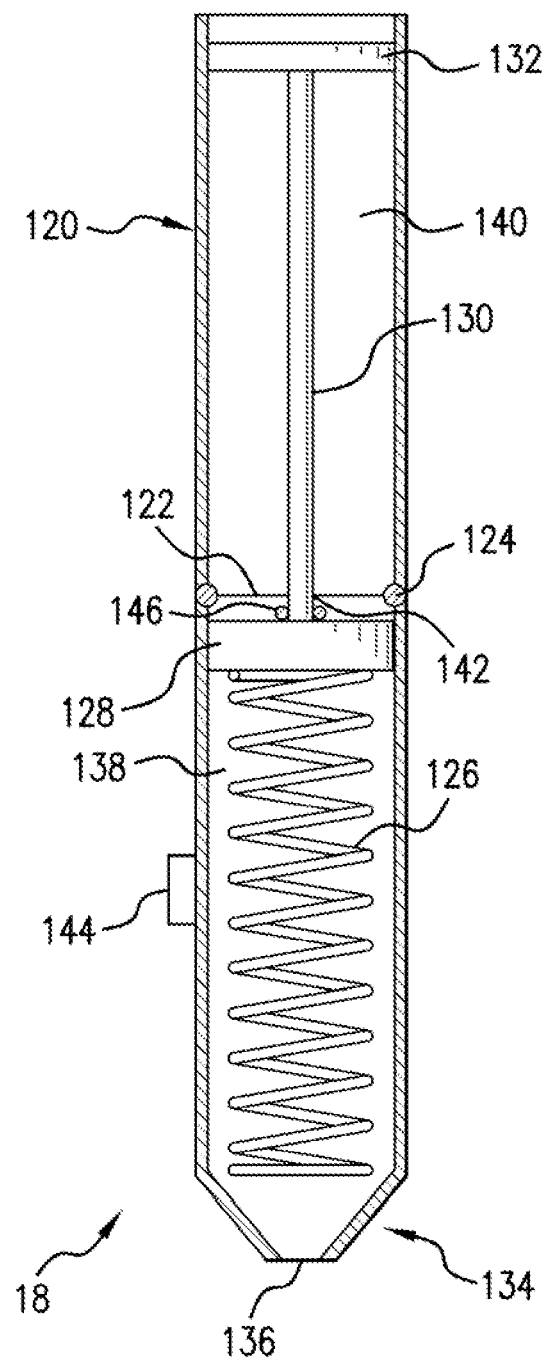
FIG. 7 is a schematic cross-sectional view of the mechanical pump assembly after actuation.

FIGS. 6 and 7 schematically depict the mechanical pump assembly 18. In the illustrated embodiment, the mechanical pump assembly 18 is a single action vacuum source used to create negative pressure in the enclosed volume 60 of the dressing 14. When the chemical pump assembly 16 is initially installed on the dressing 14 (see FIG. 8), negative pressure in the enclosed volume 60 of the dressing 14 is not created until the chemical pump assembly 16 is in full operation, i.e., until the reactor 82 scavenges the selected gas found in air from the chamber 84 and the enclosed volume 60. Therefore, the mechanical pump assembly 18 can also assist in the negative pressure maintenance of the dressing 14. Furthermore, the mechanical pump assembly 18 can assist in drawing the dressing 14 towards the dressing site 28.

In one embodiment, the mechanical pump assembly 18 may include a manually-actuated actuator and a biasing mechanism operatively connected with a movable pump element. The actuation of the manually-actuated actuator results in the biasing mechanism moving the movable pump element so as to draw air into the mechanical pump assembly. In result, negative pressure is created in the enclosed volume 60. Thus, the mechanical pump assembly 18 can be a pneumatic piston cylinder. With reference to FIG. 6, the mechanical pump assembly 18 comprises a mechanical pump housing 120, and a pump chamber having a first chamber 138 and a second chamber 140. An actuator 144 may be disposed on the side of the mechanical pump housing 120. The actuator 144 can be manually operated and used to activate the operation of the mechanical pump assembly 18. Examples of such actuators include, but are not limited to, a button, a switch, or a trigger.

An internal wall 122 may be used to separate the first chamber 138 from the second chamber 140. The internal wall 122 includes a rod opening 142 for accepting a piston rod 130. A seal 124 encircles the internal wall 122 to prevent any gas from passing between the first chamber 138 and the second chamber 140 around the internal wall 122. Alternatively, the internal wall 122 can be integrally formed with the mechanical pump housing 120. Furthermore, a second seal 146 in the rod opening 142 can enclose the piston rod 130 so that gas is prevented from passing between the first chamber 138 and the second chamber 140 through the rod opening 142 without restricting the movement of the piston rod 130.

The mechanical pump housing 120 includes a tip 134 disposed at the bottom. The tip 134 includes a tip opening 136 in fluid communication with the first chamber 138. Furthermore, the mechanical pump assembly 18 can also be in fluid communication with the opening 48 on the drape 40 via the hose 62 that can connect with the tip 134 or via the tip connecting directly with the fitting 44. The hose 62 can be any length, thus a long hose 62 can be utilized. Therefore, the mechanical pump assembly 18 can be operated on the dressing 14 before the chemical pump assembly 16 is installed on the dressing 14. This can help seal the dressing 14 at the dressing site 28. In result, the mechanical pump assembly 18 can directly apply reduced pressure to the dressing 14.

In the illustrated embodiment, the biasing mechanism is a spring 126, and the movable element is a piston 128. The spring 126 and the piston 128 are disposed in the first chamber 138. Before the mechanical pump assembly 18 is activated, a majority of the piston rod 130 is also located in the first chamber 138. Also, a head 132 disposed on the top of the piston rod 130 is disposed in the second chamber 140. When the mechanical pump assembly 18 is introduced to the first valve 92 (FIG. 9) of the chemical pump assembly 16 or connected with the fitting 44 by the hose 62 (FIG. 3), the actuator 144 is used to activate the operation of the mechanical pump assembly 18. As the mechanical pump assembly 18 is activated, a connector 170 (see FIG. 6) between the actuator 144 and the piston rod 130 releases the piston rod 130, and air enters first chamber 138 of the mechanical pump housing 120 through the tip opening 136. The connector 170 can reengage the piston rod 130. Thus, the mechanical pump assembly 18 may be reusable. As depicted in FIG. 7, the spring 126 biases the piston 128 toward the internal wall 122, which draws air into the first chamber 138. The piston rod 130 moves into the second chamber 140, and the head 132 moves towards the top surface of the mechanical pump housing 120. As a result, the negative pressure of the dressing 14 is created.

The negative pressure assembly can be susceptible to reaching a negative pressure below the target pressure range, e.g. too much vacuum or negative pressure may be achieved in the enclosed volume 60. In order to maintain the target pressure range, as shown in FIG. 5, a relief valve 148 may be disposed on the chemical pump housing 80 to release pressure as needed. Alternatively, a relief valve similar in operation to the relief valve 148 can be disposed on the drape 40 of the dressing 14. The relief valve 148 can be any valve that can manually or automatically release pressure as needed. FIG. 5 depicts one embodiment in which the relief valve 148 is disposed on the chemical pump assembly 16. It is to be understood that the relief valve 148 functions similarly in an embodiment in which the relief valve 148 is disposed on the dressing 14. Referring to FIG. 5, the relief valve 148 comprises a flexible cap 160 protruding into the chemical pump housing 80 connected with a post 162. The flexible cap 160 normally covers an opening 164. The flexible cap 160 can be made from an elastic material. As a pressure differential between ambient and the dressing 14 or ambient and the chamber 84 in the chemical pump assembly 16 moves outside of a predetermined pressure range, which can be set for example between 50 mmHg and 200 mmHg, the flexible perimeter 190 of the flexible cap 160 is drawn into the chemical pump housing 80 or the drape 40. As the flexible perimeter 190 of the flexible cap 160 is drawn toward the inside of the chemical pump housing 80 or the dressing 14, a space is created around the perimeter of the flexible cap 160 so that air can pass through the opening 164. When the opening 164 is not covered by the flexible cap 160, air from the ambient enters the chemical pump assemble 16 or the dressing 14 until the internal pressure reaches the pressure at which the perimeter 190 of the flexible cap 160 relaxes onto the inner surface of the chemical pump housing 80 to reseal and close the opening 164. The chemical pump assembly 16 and/or the dressing 14 are then subject to the amount of negative pressure at which the relief valve 148 reseals, which can be different than the pressure differential at which the opening 164 is opened while still being within the therapeutic range, e.g., between 50 mmHg and 200 mmHg.

Figure 5A:
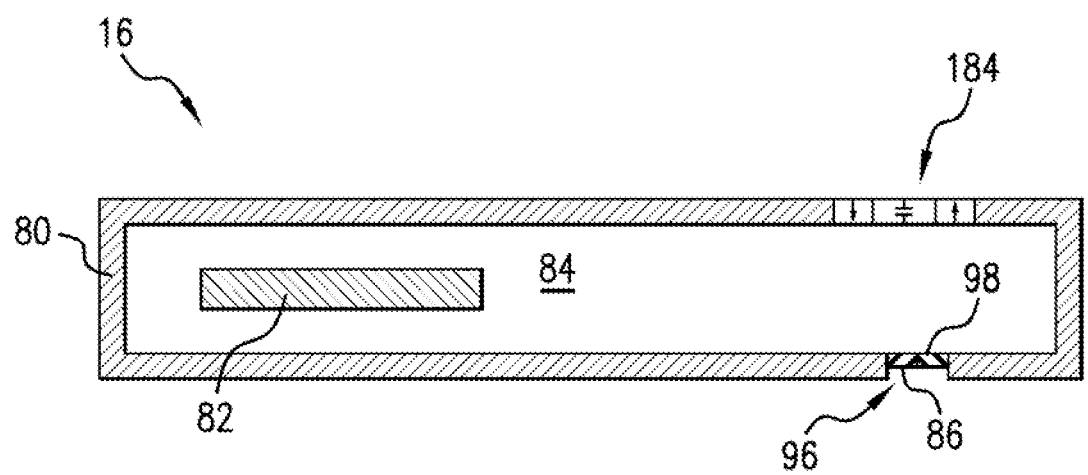
FIG. 5A is a schematic cross-sectional view of the chemical pump assembly according to yet another embodiment.
Figure 15:
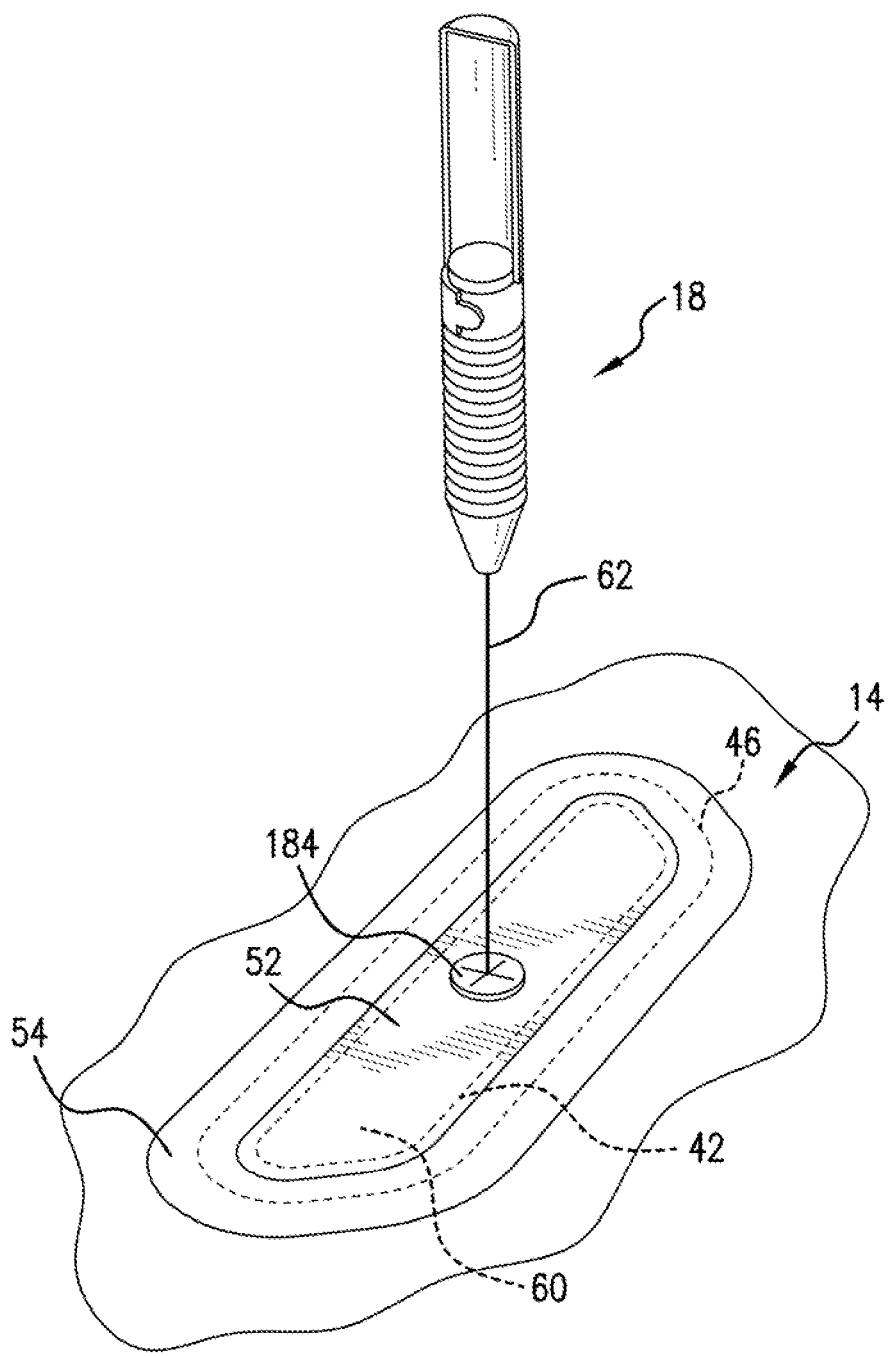
FIG. 15 is a perspective view of the mechanical pump assembly (in schematic cross-section) and the dressing after connection of the mechanical pump assembly to dressing, but before the actuation of the mechanical pump assembly according to still another embodiment.

In another embodiment, a bidirectional valve 184 is disposed on the chemical pump housing 80 instead of the first valve 192 and the release valve 148, as depicted in FIG. 5A. Alternatively, the bidirectional valve 184 can be disposed on the at least one dressing 14. In yet another embodiment, the bidirectional valve 184 may be similar construction to the valve described in U.S. Pat. No. 5,439,143. The chemical pump assembly 16 may be in fluid communication with the enclosed volume 60 through the bidirectional valve 184. Additionally, the mechanical pump assembly 18 may also be in fluid communication with the enclosed volume 60 through the bidirectional valve 184. As depicted in FIG. 15, the hose 62 can be attached to the mechanical pump assembly 18 and inserted into the bidirectional valve 184. In result, the mechanical pump assembly 18 is in fluid communication with the enclosed volume 60.

The bidirectional valve 184 may include three operating states. In the first operating state, gas is allowed to exit the chamber 84 and/or the enclosed volume 60 through the bidirectional valve 184 when the external pressure is below that of the enclosed volume 60 and/or the chamber 84. In the second operating state, the bidirectional valve 184 precludes gas from entering or exiting the enclosed volume 60 and/or the chamber 84 through the bidirectional valve 184 when the pressure of the chamber 84 and/or the enclosed volume 60 is between the first predetermined threshold and a second predetermined threshold. In the third operating state, the bidirectional valve 184 allows gas from ambient to enter the enclosed volume 60 and/or the chamber 84 through the bidirectional valve 184 when the pressure in the enclosed volume 60 and/or the chamber 84 is below the predetermined threshold. In one embodiment, the predetermined threshold is 560 mmHg or 200 mmHg below atmospheric. In yet another embodiment, the bidirectional valve 184 may include springs that automatically actuate the bidirectional valve 184 when a pressure differential is at the first or second predetermined threshold.

Figure 14:
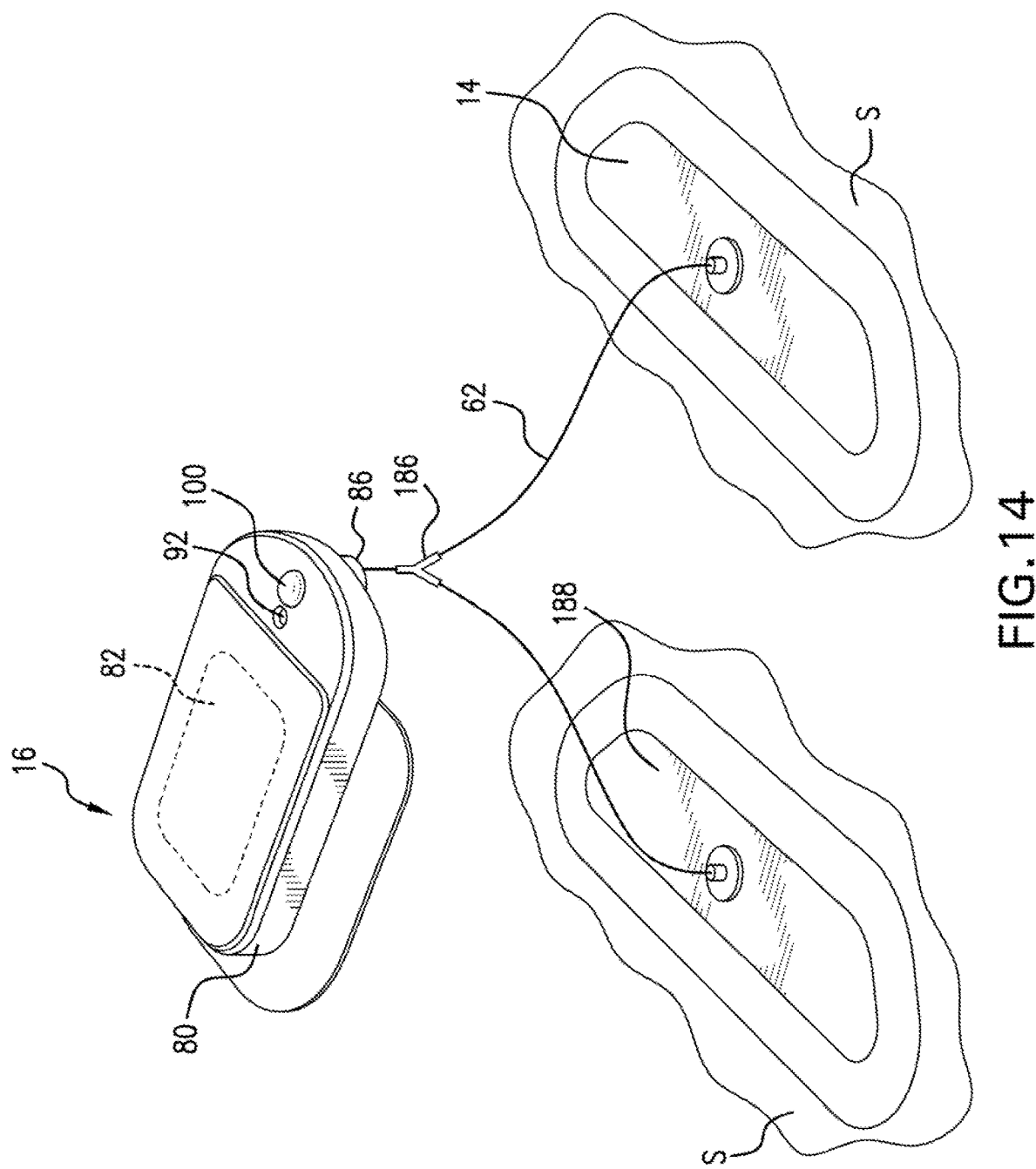
FIG. 14 is a perspective view of the chemical pump assembly and the dressing and a second dressing after negative pressure in a therapeutic range underneath the dressing according to another embodiment.

In still another embodiment, the mechanical pump assembly 18 is connected to multiple dressings. Furthermore, the mechanical pump assembly 18 can be connected to the multiple dressings at the same time. For example, the mechanical pump assembly 18 can be connected to a second dressing 188. The hose 62 can include a Y-shaped fitting 186 to connect the mechanical pump assembly 18 to the dressing 14 and the second dressing 188 at the same time. Furthermore, the chemical pump assembly 16 can also be connected to multiple dressings and can be connected to the multiple dressings at the same time. As depicted in FIG. 14, the hose 62 can include the Y-shaped fitting 186 to simultaneously connect the chemical pump assembly 16 to the dressing 14 and the second dressing 188.

A method for achieving negative pressure therapy with the negative pressure kit 10 will be described hereinafter. First, at least one dressing 14 is removed from the tray kit 12, and the drape release liner is removed to expose the adhesive 66 on the bottom surface of the drape edge 54. The drape edge 54 is placed on skin S around at least one dressing site 28 and is secured to the skin S by the adhesive 66.

Figure 8:
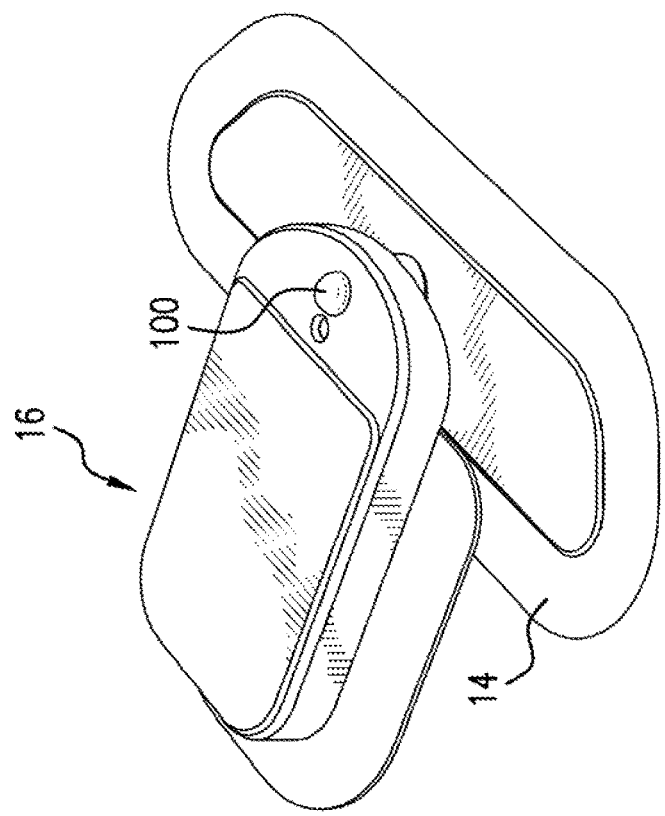
FIG. 8 is a perspective view of the dressing and the chemical pump assembly after connection of the chemical pump assembly to the dressing, but prior to negative pressure in a therapeutic range underneath the dressing.

With reference to FIG. 8, the drape 40 is secured over the dressing site 28, and the second valve 96 on the chemical pump assembly 16 is introduced to the fitting 44 on the drape 40. The second valve 96 is placed over the fitting 44, and the flaps 98 are opened. When the flaps 98 are open, the chemical pump assembly 16 is in fluid communication with the dressing 14. The reactor 82 begins to consume the selected gas from the enclosed volume 60 but is not complete at this time.

Figure 9:
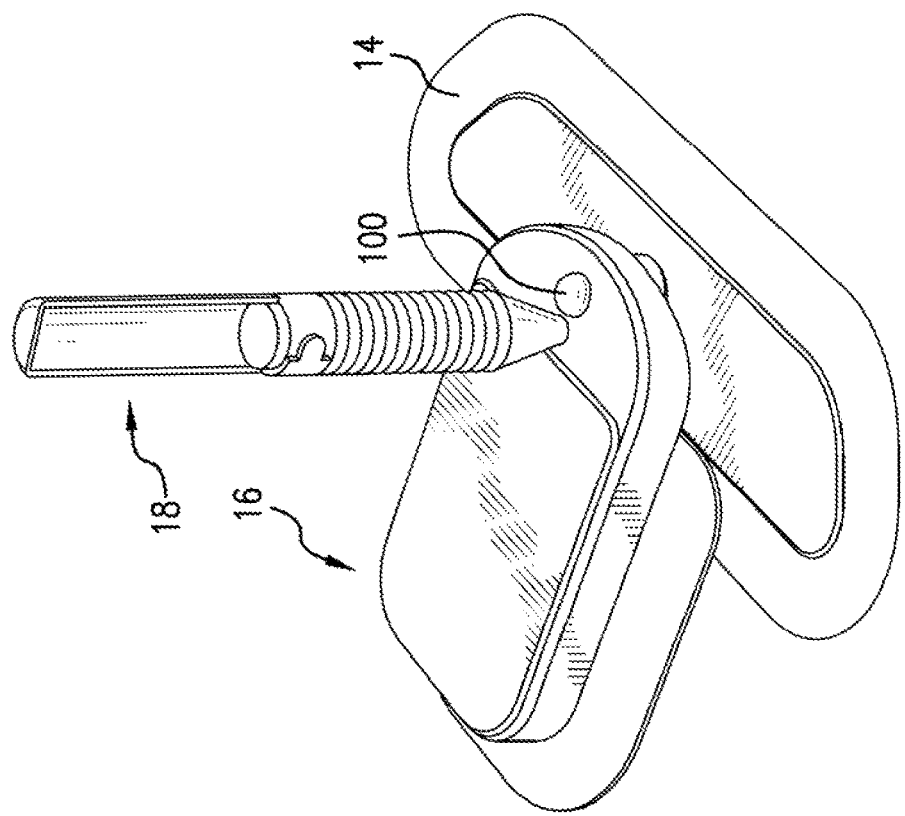
FIG. 9 is a perspective view of the dressing, the chemical pump assembly and the mechanical pump assembly (in schematic cross-section) after connection of the chemical pump assembly to the dressing and connection of the mechanical pump assembly to the chemical pump assembly, but prior to actuation of the mechanical pump assembly.
Figure 11:
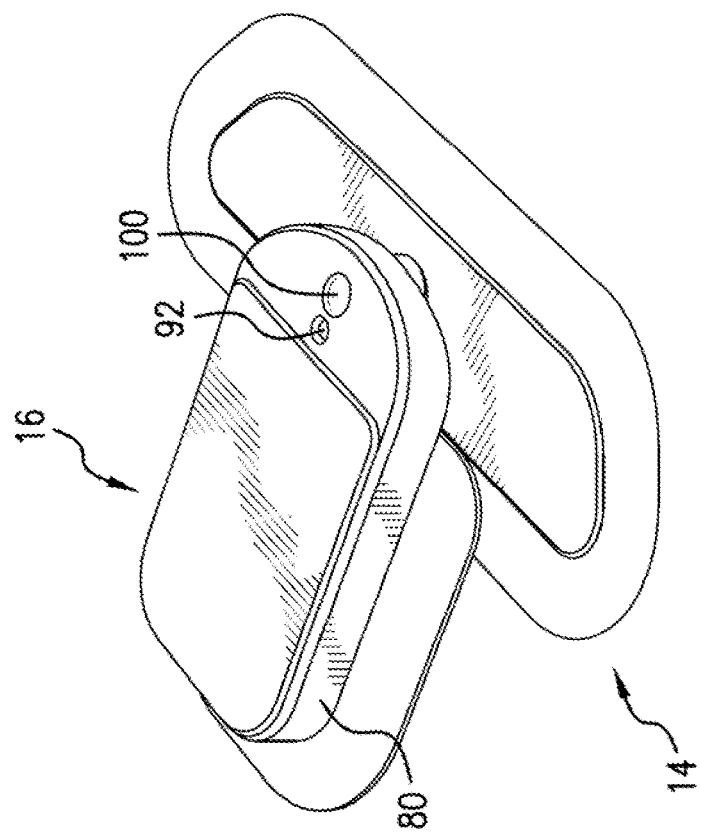
FIG. 11 is a perspective view of the dressing and the chemical pump assembly after connection of the chemical pump assembly to the dressing, and after negative pressure in a therapeutic range has been achieved underneath the dressing and a diaphragm inverts toward a chamber in the chemical pump assembly.
Figure 10:
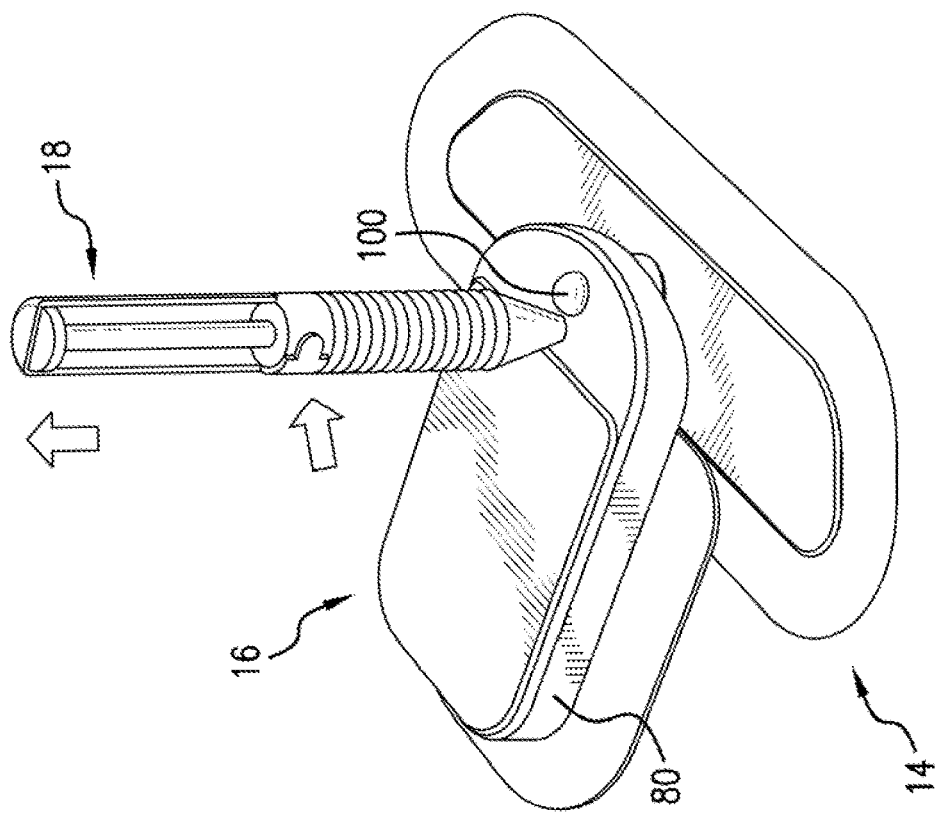
FIG. 10 is a perspective view of the dressing, the chemical pump assembly and the mechanical pump assembly after connection of the chemical pump assembly to the dressing and connection of the mechanical pump assembly to the chemical pump assembly, and after actuation of the mechanical pump assembly after actuation.

Afterwards, the mechanical pump assembly 18 is inserted into the first valve 92 disposed on the chemical pump assembly 16 to open the flaps 94, as depicted in FIG. 9. As the flaps 94 are opened, the mechanical pump assembly 18 is in fluid communication with the chamber 84 in the chemical pump assembly 16. Alternatively, the mechanical pump assembly 18 is inserted into the bidirectional valve 184. Also, the mechanical pump assembly 18 is in fluid communication with the enclosed volume 60 via the chemical pump assembly 16. When the mechanical pump assembly 18 is in fluid communication with the chemical pump assembly 16, the actuator 144 is used to activate the operation of the mechanical pump assembly 18, as depicted in FIG. 10. Then, the spring 126 pushes the piston 128 towards the internal wall 122. As the piston 128 moves, air enters the first chamber 138 of the mechanical pump assembly 18, and the dressing 14 is drawn toward the skin S. The mechanical pump assembly 18 is then removed, and the flaps 94 of the first valve 92 are closed by their resilient forces, as depicted in FIG. 11. In the embodiment with the bidirectional valve 184, the bidirectional valve 184 moves to the second operating state, as the mechanical pump assembly 18 is removed from the bidirectional valve 184. The reactor 82 in the chemical pump assembly 16 can continue to apply or maintain reduced pressure to the dressing 14. In result, the pressure in the dressing 14 is reduced to a negative pressure, and the negative pressure indicator 100 signals when the negative pressure has been achieved. At any time the reduced pressure decreases below a target pressure range, the relief valve 148 or the bidirectional valve 184 releases pressure as needed to restore the reduced pressure to a predetermined pressure differential.

In another embodiment, the mechanical pump assembly 18 can be inserted prior to the chemical pump assembly 16. First, the at least one dressing 14 is placed and secured over the at least one dressing site 28. Then, the mechanical pump assembly 18 is connected to the fitting 44 on the dressing 14 by the hose 62. Alternatively, the first valve 92 or bidirectional valve 184 is disposed on the dressing 14 instead of the chemical pump assembly 16 to provide direct fluid communication between the dressing 14 and the mechanical pump assembly 18. As a result, the mechanical pump assembly 18 is in fluid communication with the enclosed volume 60. The first valve 92 or bidirectional valve 184 may further replace the fitting 44. In these alternate embodiments, the mechanical pump assembly 18 is inserted into the first valve 92 or the bidirectional valve 184 on the dressing 14.

After the mechanical pump assembly 18 is connected to the dressing 14, the mechanical pump assembly 18 is activated with the actuator. In result, the piston 128 moves toward the internal wall 122, and air enters the first chamber 138 of the mechanical pump assembly 18. The mechanical pump assembly 18 is removed and replaced by the chemical pump assembly 16. The reactor 82 in the chemical pump assembly 16 begins reacting with a selected gas found in air to maintain the negative pressure of the dressing. When the negative pressure in the enclosed volume 60 is achieved, the indicator on the dressing 14 and/or the chemical pump assembly 16 signals when the dressing 14 reaches a negative pressure. As needed, the relief valve 148 or the bidirectional valve 184 releases pressure when the reduced pressure decreases below a target pressure range.

Figure 12:
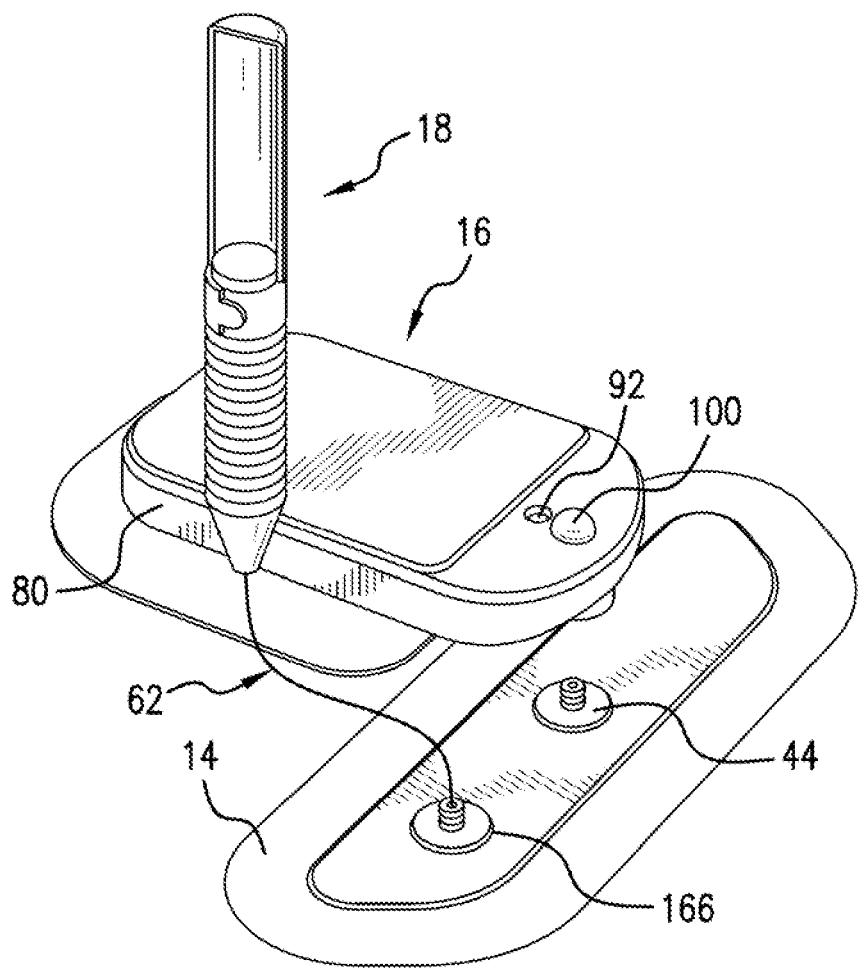
FIG. 12 is a perspective view of the dressing, the chemical pump assembly and the mechanical pump assembly before connection of the chemical pump assembly to the dressing and after connection of the mechanical pump assembly to the dressing, but prior to actuation of the mechanical pump assembly.

In still another embodiment, the chemical pump assembly 16 and the mechanical pump assembly 18 are both connected to the at least one dressing 14. In this embodiment, a first valve, fitting, or hose and a second valve, fitting or hose are disposed on the dressing 14. The chemical pump assembly 16 is connected to the dressing via the first valve, fitting, or hose. The mechanical pump assembly 18 is connected for the second valve, fitting, or hose. For example, the chemical pump assembly 16 is connected to the dressing 14 via the fitting 44 disposed on the dressing 14, while the mechanical pump assembly 18 is connected to the dressing 14 via the hose 62 and a second fitting 166 disposed on the dressing 14, as depicted in FIG. 12. Also, in particular when the dressing 14 that includes at least one relief valve similar to the relief valve 148 described above, the chemical pump assembly 16 could be replaced with an electromechanical pump similar to those now used with known negative pressure wound therapy devices. Different than known negative pressure wound therapy devices, however, the relief valve(s) on the dressing 14 can open and close (as described above) to maintain the enclosed volume underneath the dressing within the therapeutic range. Also, in lieu of the relief valves, the dressing 14 could include a bidirectional valve similar to the bidirectional valve 184 that could cooperate with the mechanical pump assembly 18 while an electro-mechanical pump similar to those now used with known negative pressure wound therapy devices could connect with the fitting 44 shown in FIG. 12.

Figure 13:
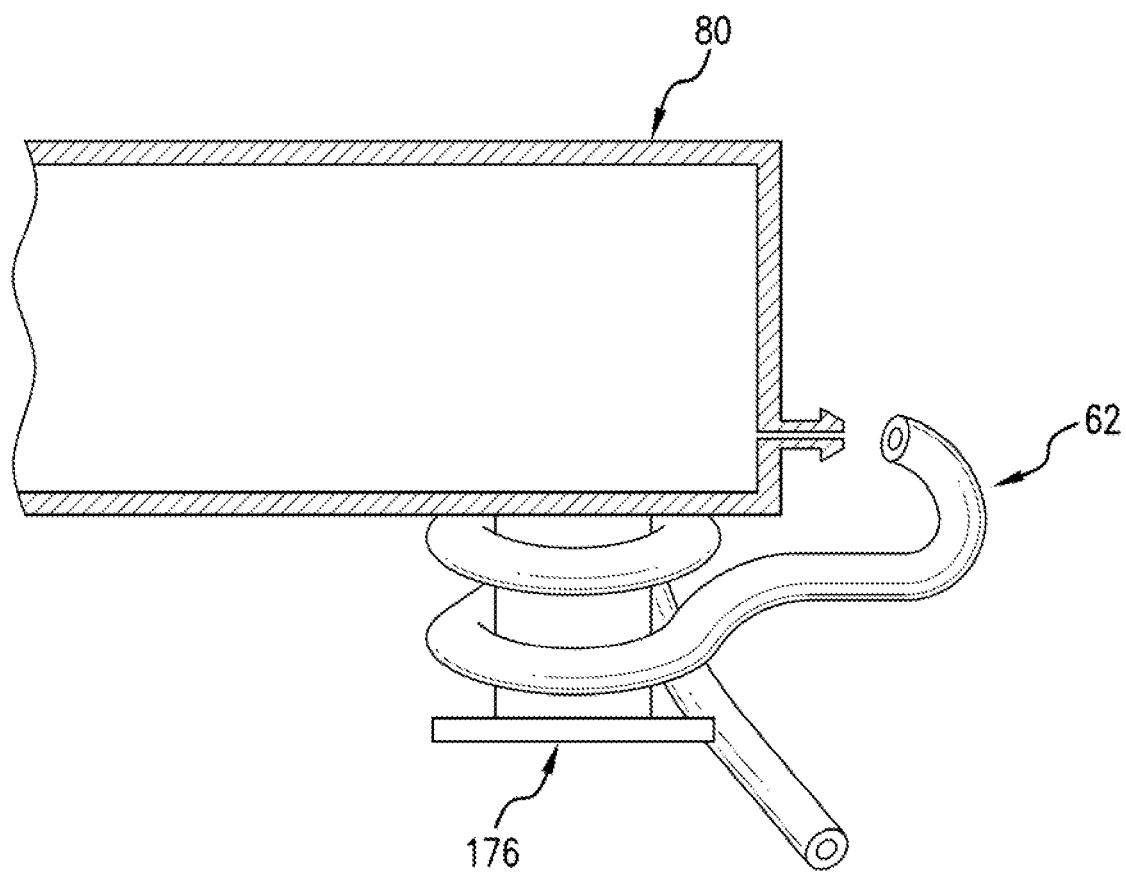
FIG. 13 is schematic cross-sectional view of a portion of a chemical pump housing including a wrap element.

Furthermore, at least one attachment can be disposed on the mechanical pump assembly 18 or the chemical pump assembly 16 for storing the hose 62. An example of such an attachment is, but is not limited to, a wrap element. With reference to FIG. 13, the chemical pump assembly 16 may include a wrap element 176 disposed on the chemical pump housing 80 around which the hose 62 can be wound. Alternatively, the wrap element 176 can be disposed on the mechanical pump housing 120. The hose 62 can be coiled around the at least one attachment so that the hose 62 is secured during storage and transportation. In another embodiment, the hose 62 can retract into the chemical pump assembly 16. In yet another embodiment, the hose 62 can retract into the mechanical pump assembly 18. Alternatively, the tray kit 12 can include an additional recess for storing the hose 62.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A negative pressure assembly comprising:
a drape for covering a dressing site on a patient and capable of maintaining a negative pressure underneath the drape when sealed against skin upon application of a vacuum;
a sealing element that when applied to the skin cooperates with the drape to define an enclosed volume covered by the drape and surrounded by the sealing element;
a reactor located with respect to the drape and the sealing element so as to be in fluid communication with the enclosed volume when the drape is covering the dressing site, the reactor being configured to react with a selected gas found in air so as to consume the selected gas;
a mechanical pump assembly including a pump chamber fluidly connectable to the enclosed volume, and configured to draw air from the enclosed volume into the pump chamber when fluidly connected with the enclosed volume; and
a chemical pump assembly including a chemical pump housing and the reactor positioned in a chamber of the chemical pump housing, wherein the mechanical pump assembly is connectable to the chemical pump assembly so that the pump chamber is in fluid communication with the enclosed volume via the chemical pump assembly.

2. The negative pressure assembly of claim 1, further comprising a dressing including an absorbent material and the drape.

3. The negative pressure assembly of claim 2, further comprising a relief valve on the dressing in fluid communication with the enclosed volume and ambient, the relief valve being configured to allow gas from ambient to enter the enclosed volume through the relief valve when a pressure differential between ambient and the enclosed volume is outside a predetermined pressure range.

4. The negative pressure assembly of claim 1, wherein the chemical pump assembly is connectable with the dressing via a fitting, such that the chamber of the chemical pump housing is in fluid communication with the enclosed volume.

5. The negative pressure assembly in claim 1, further comprising a diaphragm on the chemical pump housing configured to move toward the chamber of the chemical pump housing when the chamber is under negative pressure.

6. The negative pressure assembly in claim 1, wherein the mechanical pump assembly is connectable to the chemical pump housing via a valve, a fitting, or a hose.

7. The negative pressure assembly in claim 6, wherein the valve is configured to allow gas to exit through the valve and into the pump chamber and to prevent ambient air from entering the chamber of the chemical pump housing through the valve.

8. The negative pressure assembly of claim 1, further comprising a relief valve on the chemical pump housing in fluid communication with the chamber of the chemical pump housing and ambient, the relief valve being configured to allow gas from ambient to enter the chamber through the relief valve when a pressure differential between ambient and the chamber is outside a predetermined pressure range.

9. The negative pressure assembly in claim 1, wherein the chemical pump assembly is connectable to a second dressing covering a second dressing site via a valve, a fitting, or a hose.

10. A negative pressure assembly, comprising:
a drape for covering a dressing site on a patient and capable of maintaining a negative pressure underneath the drape when sealed against skin upon application of a vacuum;
a sealing element that when applied to the skin cooperates with the drape to define an enclosed volume covered by the drape and surrounded by the sealing element;
a reactor located with respect to the drape and the sealing element so as to be in fluid communication with the enclosed volume when the drape is covering the dressing site, the reactor being configured to react with a selected gas found in air so as to consume the selected gas;
a mechanical pump assembly including a pump chamber fluidly connectable to the enclosed volume, and configured to draw air from the enclosed volume into the pump chamber when fluidly connected with the enclosed volume, and
a chemical pump assembly including a chemical pump housing and the reactor positioned in a chamber of the chemical pump housing, wherein the mechanical pump assembly is connectable to the chemical pump assembly so that the pump chamber is in fluid communication with the enclosed volume via the chemical pump assembly,
wherein the mechanical pump assembly includes a manually-actuated actuator and a biasing mechanism operably connected with a movable pump element, wherein actuation of the manually-actuated actuator results in the biasing mechanism moving the movable pump element so as to draw air into the mechanical pump assembly.

11. The negative pressure assembly of claim 10, further comprising a relief valve on the chemical pump housing in fluid communication with the chamber of the chemical pump housing and ambient, the relief valve being configured to allow gas from ambient to enter the chamber of the chemical pump housing through the relief valve when a pressure differential between ambient and the chamber of the chemical pump housing is outside a predetermined pressure range.

* * * * *